United States Patent
Schwab

(10) Patent No.: US 7,785,298 B2
(45) Date of Patent: Aug. 31, 2010

(54) METHOD AND APPARATUS FOR CO-INJECTION

(76) Inventor: Lester M. Schwab, P.O. Box 2880, Danville, CA (US) 94526-7880

( * ) Notice: Subject to any disclaimer, the term of this patent is extended or adjusted under 35 U.S.C. 154(b) by 207 days.

(21) Appl. No.: 11/750,183

(22) Filed: May 17, 2007

(65) Prior Publication Data
US 2008/0287913 A1  Nov. 20, 2008

(51) Int. Cl.
*A61M 5/315* (2006.01)
(52) U.S. Cl. .................... 604/218; 604/57; 604/60
(58) Field of Classification Search .......... 604/57–64, 604/116–118, 218–231, 239, 82–92
See application file for complete search history.

(56) References Cited

U.S. PATENT DOCUMENTS

| 4,341,211 | A | * | 7/1982 | Kline | 604/514 |
| 5,288,291 | A | * | 2/1994 | Teoh | 604/60 |
| 5,370,611 | A | | 12/1994 | Niezink et al. | |
| 5,395,319 | A | | 3/1995 | Hirsch et al. | |
| 6,398,718 | B1 | * | 6/2002 | Yachia et al. | 600/29 |
| 7,338,474 | B2 | | 3/2008 | Kirk | |
| 2005/0215957 | A1 | * | 9/2005 | Hynes | 604/218 |

* cited by examiner

*Primary Examiner*—Kevin C Sirmons
*Assistant Examiner*—Phillip Gray
(74) *Attorney, Agent, or Firm*—Townsend and Townsend and Crew, LLP

(57) ABSTRACT

Systems and methods of co-injecting a solid object and an amount of fluid into a patient's tissue includes separably coupled syringe and needle portions. The syringe portion includes a barrel, a plunger, and a pushrod for disposing the solid object that is capable of independent movement with respect to the plunger. The needle portion includes a hollow needle configured to allow both the object and the fluid to pass out of the needle and into the patient's tissue. The needle portion may include a housing located behind the needle that is configured to hold the solid object. Once the needle portion and the syringe portion are coupled together, the device is operated in accordance with methods of the present invention to effectively co-inject the patient with the object and the amount of fluid.

13 Claims, 4 Drawing Sheets

US 7,785,298 B2

METHOD AND APPARATUS FOR CO-INJECTION

BACKGROUND OF THE INVENTION

The present invention relates to systems and methods of injecting a patient (human or animal) with both an object and an amount of fluid. There are many applications where it is desired that an object, such as a radio transponder, a collagen pellet, a caplet of medicine, etc., be delivered into the tissue of a patient at a particular location along with an amount of fluid. For example, such co-injection procedures may be performed to deliver pet identification microchips with a vaccine or anti-body. Some approaches to such procedures are described in Teoh U.S. Pat. No. 5,288,291 and Taylor et al. U.S. Pat. No. 5,211,129. The present invention, however, sets forth improvements on the systems and methods for co-injection.

BRIEF SUMMARY OF THE INVENTION

The present invention provides for systems and methods of co-injecting an object and an amount of fluid into a patient. An embodiment of the present invention includes separate syringe and needle portions that are coupled together. The syringe portion may be provided to a user preloaded with the amount of fluid to be injected or may be loaded with the amount of fluid at the time of the injection procedure. The syringe portion includes a plunger for ejecting the fluid and a push rod for engaging and pushing the object. The plunger and the push rod are capable of movement along a shared axis with respect to and independently of each other. The needle portion includes a hollow needle configured to allow both the object and the fluid to pass out of the needle and into the patient's tissue. The needle portion may include a housing located behind the needle that is configured to hold the object. Once the needle portion and the syringe portion are coupled together, the push rod is moved independently of the plunger to push the object toward the end of the needle and the plunger is moved in the same direction to eject the fluid from the syringe.

One aspect of the present invention is directed to an injector for simultaneously co-injecting an object and an amount of fluid. The injector includes a syringe portion that has a barrel, a plunger, and a push rod coaxially disposed about an axis. The push rod and the plunger are movable along the axis independently of each other. The barrel holds the amount of fluid in a space created by distal movement of the plunger along the axis. The injector also includes a needle portion with a needle. The needle portion is configured to hold the object and allow it to be ejected from a distal end of the needle. The needle portion is separably coupled with the syringe portion. The push rod is configured to move distally along the axis to engage the object held in the needle portion and to eject the object from the distal end of the needle. The plunger is configured to move distally along the axis to eject the amount of fluid out of the distal end of the needle.

Another aspect of the present invention is directed to a method for simultaneously co-injecting an object and an amount of fluid using an injector. The method includes coupling a needle portion holding the object with a syringe portion having the amount of fluid loaded within. The push rod is moved distally along an axis independently of the plunger coaxially disposed on the axis to distally move the object without ejecting any of the amount of fluid. After the object has been ejected the push rod and the plunger are moved together distally along the axis to eject the amount of fluid.

Further aspects and advantages of the present invention are set forth below in the detailed description of the preferred embodiments.

DETAILED DESCRIPTION OF THE INVENTION

Embodiments of the present invention provide for systems and methods of co-injecting an object and an amount of fluid into a patient. The invention is applicable to both human and non-human patients and is useful wherever it is desired to easily and near simultaneously inject an object and an amount of fluid into the tissue of the patient. An embodiment of the present invention includes a syringe portion and a needle portion. The syringe portion may be provided to a user preloaded with the amount of fluid to be injected or may be loaded with the amount of fluid at the time of the injection procedure. The syringe portion includes a barrel that holds the amount of fluid within, a plunger for moving the fluid out of the fluid dispensing end of the barrel, and a push rod for pushing the object that is capable of movement independent of the plunger. The needle portion includes a hollow needle configured to allow both the solid object and fluid to pass out of the needle and into the patient's tissue. The needle portion may include a housing located behind the needle that is configured to secure the solid object. Once the needle portion and the syringe portion are coupled together, the device is operated in accordance with methods of the present invention to effectively co-inject the patient's tissue with the object and the amount of fluid.

Figure 1:
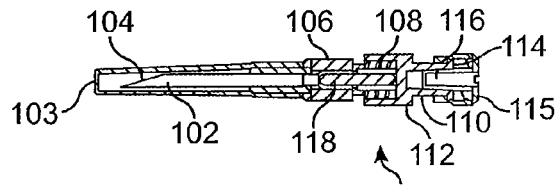
FIG. 1 illustrates a needle portion in accordance with an embodiment of the present invention.

FIG. 1 shows a needle portion in accordance with an embodiment of the present invention. Needle portion 100 has a hollow needle 102 at its distal end, which is capped with a removable needle cap 103. For purposes of the present application, the end of the device configured to be held away from the user (i.e., the needle end) is referred to as the distal end, and the opposite end is referred to as the proximal end. Needle 102 includes a beveled needle tip 104 which may be sharp to aid in tissue penetration. A needle hub 106, which includes a hollow channel for communicating with the hollow channel of needle 102, is disposed immediately behind needle 102 (i.e., proximally of the needle). Needle hub 106 includes a male luerlock 108 at its proximal end for creating a fluid tight connection. Needle 102 and hub 106 are generally manufactured together in commercially available needles.

A housing 110 may be disposed immediately behind or proximally of hub 106 and includes a female luerlock 112 at its distal end for engaging male luerlock 108 of the needle hub 106. Housing 110 includes, at its proximal end, a male luerlock 114 for creating a fluid tight connection with a syringe that has a female luerlock at its fluid dispensing end. Housing 110 includes chamber 116 configured to securely hold object 118. Object 118 may be entirely contained within the chamber 116 or may also be partially disposed within the hollow channel of hub 106. Male luerlock 114 may be used to engage an end cap 115 having a female luerlock. Cap 115 is used to ensure that object 118 stays within the housing until the cap is removed at the time of the procedure. Alternatively, a plastic membrane (not shown) may be used to seal off the proximal end of housing 110.

Figure 1A:
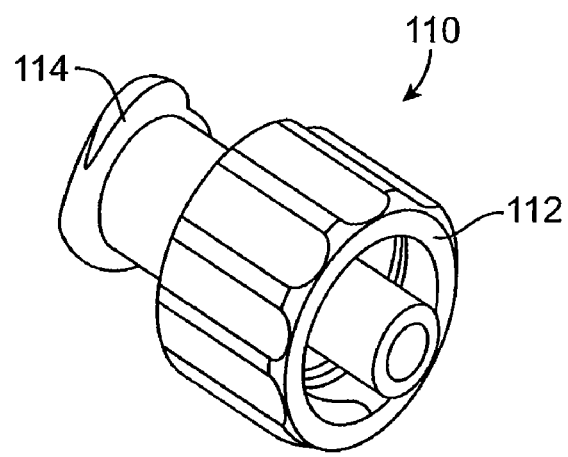
FIG. 1A is a perspective view of a housing in accordance with an embodiment of the present invention.
Figure 1B:
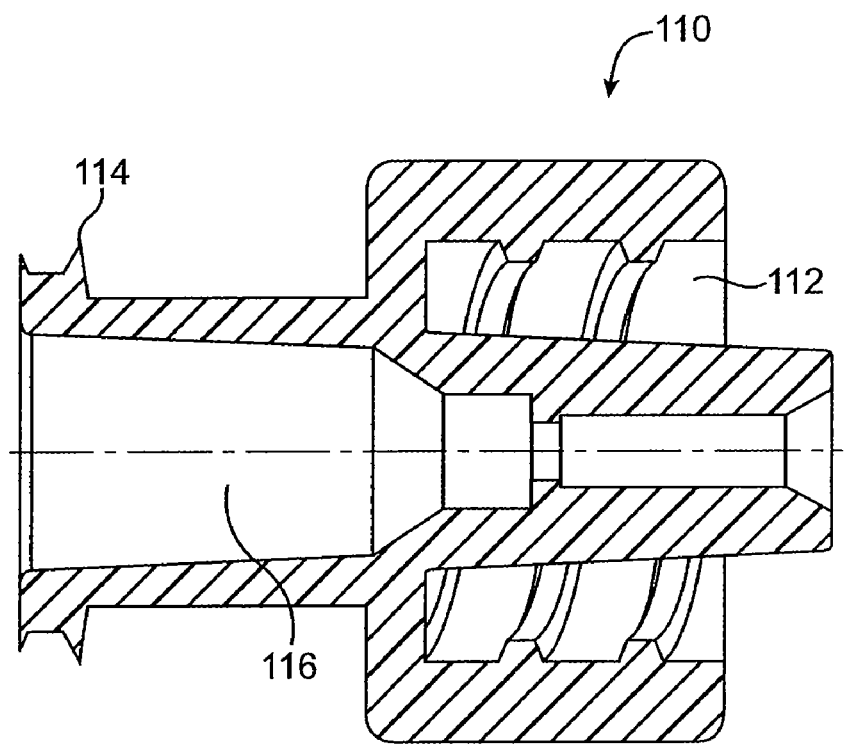
FIG. 1B is a cross-sectional view of the housing.

FIG. 1A is a perspective view of a housing 110 and FIG. 1B is a cross section showing the interior details of its parts. Object 118 may be secured within chamber 116 by using an adhesive, by using a friction fit, or by using other suitable connection known to those in the art. Object 118 may be an electronic marker or transponder, a plug of collagen (which may be combined with a metallic radiology marker), a caplet of medication, a pellet containing a fluid or gel (which may be punctureable), a solid, semi-solid, gel, or any other desired material distinguishable from the fluid to be injected. It should be understood that housing 110 is optional and need not be included in some embodiments, in which case the object 118 may be disposed and/or secured within the hollow needle 102 or the needle hub 106. In one embodiment of the invention, needle portions 100 may be packaged and delivered in the state shown in FIG. 1.

Figure 2:
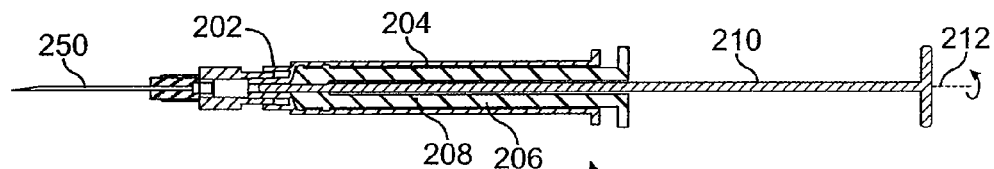
FIG. 2 illustrates a syringe portion in accordance with an embodiment of the present invention coupled with a conventional small-gauge needle (e.g., for drawing a fluid into the syringe).

FIG. 2 illustrates a syringe portion in accordance with an embodiment of the present invention that is assembled with a conventional needle. Syringe portion 200 is shown having a conventional small-gauge needle 250 (e.g., 20 gauge) attached to its fluid-dispensing end 202. Such a small-gauge needle is used to draw an amount of fluid to be co-injected with object 118 into the syringe portion 200. Fluid-dispensing end 202 includes a female luerlock for receiving male luerlock 114 or 108 of the needle portion. As shown in FIG. 2, syringe portion 200 includes a conventional syringe barrel 204 configured to hold an amount of fluid within. Syringe plunger 206 is disposed coaxially within barrel 204 and is unconventional in that it includes a hollow channel 208 along its central axis 212 for receiving a push rod 210. Channel 208 extends over the entire length of the plunger 206 and enables push rod 210 to slideably move along the axis 212 with respect to the plunger 206. That is, push rod 210 can be moved independently of plunger 206 along axis 212, and vice versa. As shown in FIG. 2, no fluid has yet been drawn into syringe barrel 204. Push rod 210 protrudes from the distal end of hollow channel 208 and is positioned substantially adjacent fluid-dispensing end 202 of the syringe.

Figure 2A:
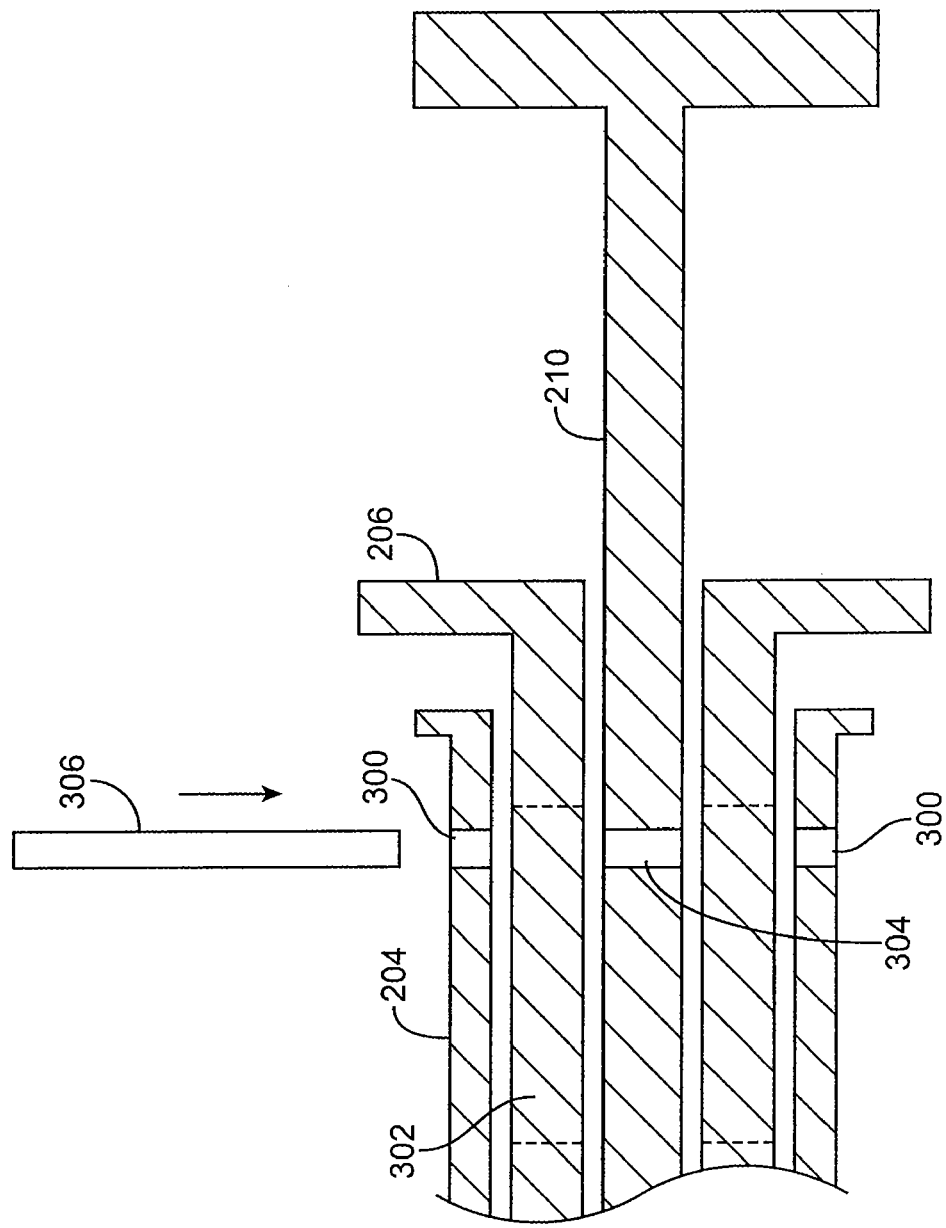
FIG. 2A illustrates a syringe portion in accordance with an embodiment of the present invention adapted with a pin for preventing inadvertent movement of the push rod.
Figure 2B:
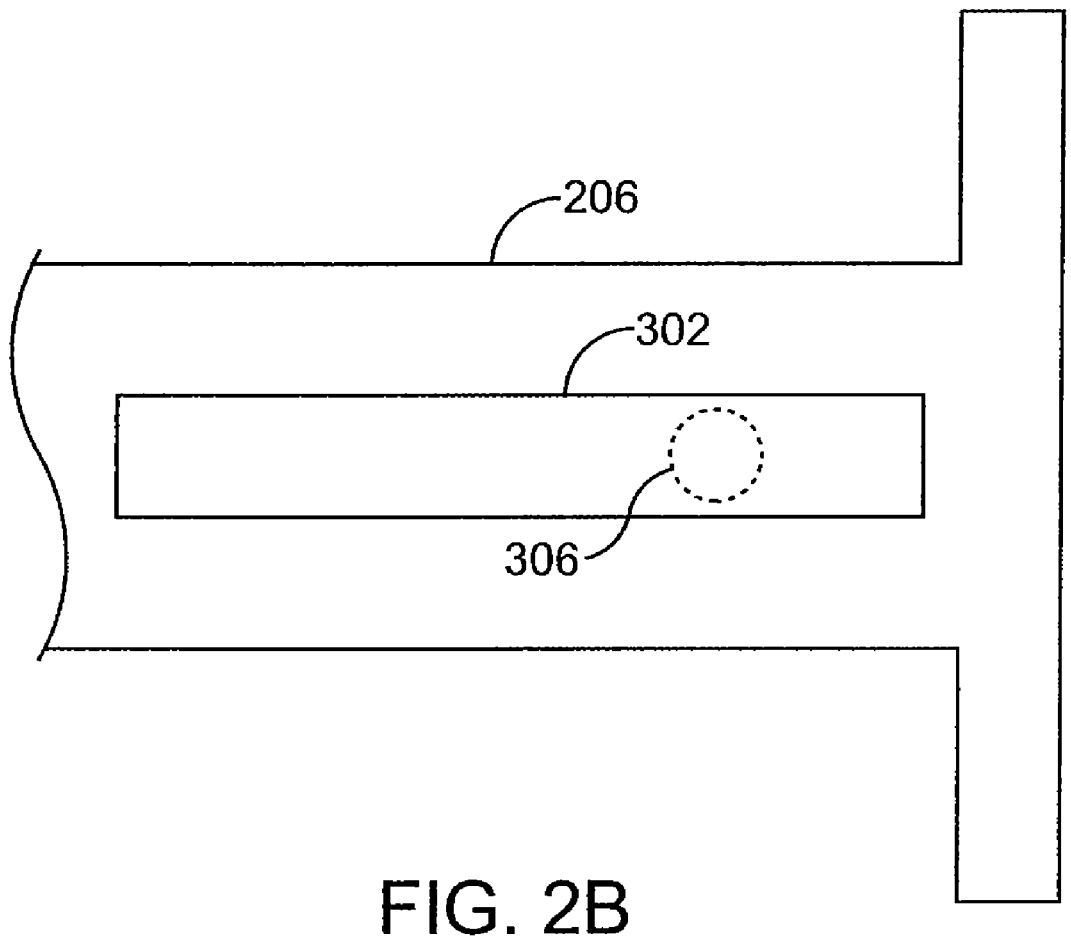
FIG. 2B illustrates a slot provided in the plunger of FIG. 2A.

FIG. 2A is cross-sectional view showing one embodiment of syringe portion 200 adapted with a pin for preventing inadvertent movement of push rod 210. As shown in FIG. 2A, opposing pin holes 300 are provided in barrel 204. A slot 302 is provided through the plunger 206 to accommodate a pin 306. As shown in FIG. 2B, which is a view of plunger 206 from the top of FIG. 2A, slot 302 accommodates pin 306 and enables the plunger 206 to move over pin 306 while push rod 210 is held stationary. Returning to FIG. 2A, hole 300 corresponds to a pin hole 304 in the push rod 210 when the push rod is in its initial state (shown here and in FIG. 2). Pin 306 is placed into hole 300, through slot 302, into hole 304 of the push rod, and out through hole 300 on the opposite side of the syringe barrel 200. When the pin 306 is installed the push rod 210 is held in its initial state. This approach eliminates any inadvertent movement of the push rod 210, but still enables plunger 206 to move rearward along slot 302 to draw fluid into the syringe or, subsequently, forward along the slot 302 to eject air from the syringe Pin 306 can be removed when movement of push rod 210 is desired, as will be described in detail below.

Figure 3:
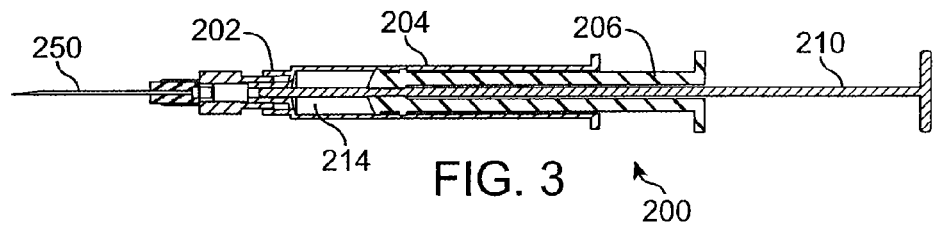
FIG. 3 illustrates a syringe portion in accordance with an embodiment of the present invention coupled with a conventional small-gauge needle and having an amount of fluid within its barrel.

FIG. 3 illustrates syringe portion 200 when an amount of fluid 214 has been drawn into the syringe barrel 204. In one preferred embodiment, the amount of fluid 214 is about 1 cc of fluid. It should be understood that, given the diameter of the syringe barrel used, a given amount of drawn fluid translates into a set distance that the plunger 206 is drawn back. Fluid 214 may be a vaccine, an antibiotic, an antiseptic, an anti-inflammatory, a saline solution, or any other safe and suitable fluid. Fluid 214 may serve to treat an area in which the injection is made, may serve as a carrier fluid that aids in the delivery of the object 118 by helping to propel the object out of needle 102, and/or may serve to provide capillary attraction that prevents migration of the object. Returning to FIG. 3, it should be noted that plunger 206 has been drawn back independently of the push rod 210, which remains in the same position as it had in FIG. 2. In one embodiment of the invention, syringe portion 200 may be packaged and delivered in the state shown in FIG. 3 (but without small-gauge needle 250 attached and with a cap over fluid-dispensing end 202 to prevent leakage of fluid). Syringe portions 200 may be prepackaged with an array of different fluids to be matched with an appropriate needle portion 100 having the desired object 118 (e.g., a combination of an antibiotic syringe portion 200 with a transponder needle portion 100 may be used to inject a pet for identification purposes). Alternatively, syringe portion 200 may be filled with a desired amount of fluid 214 through small-gauge needle 250 at the time of the injection procedure.

Figure 4:
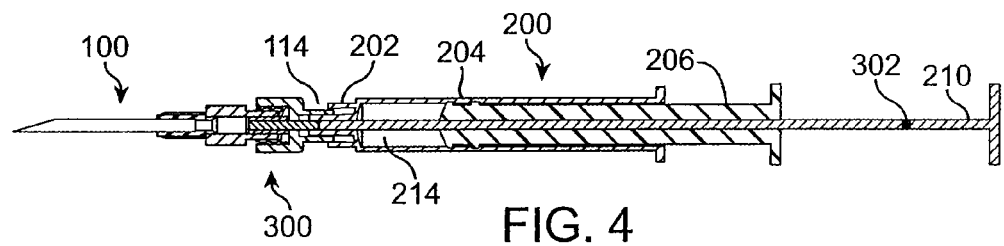
FIG. 4 illustrates a combined device in accordance with an embodiment of the present invention in an initial state formed by the syringe portion and the needle portion including the object to be ejected and with the amount of fluid within the syringe barrel.

In one embodiment of the invention illustrated by FIG. 4, the user attaches the needle portion 100 to syringe portion 200 (having the amount of fluid 214 within) to create a combined device 300. In the approach where the small gauge needle 250 is used to draw the amount of fluid, the needle 250 is removed from the syringe portion 200 and is disposed of in a conventional way before needle portion 100 is attached. For example, male luerlock 114/108 of the needle portion is engaged with distal end 202 of the syringe portion to create a fluid-tight connection between the two portions 100 and 200. In one preferred method of operation illustrated by FIG. 5, the user arms the device 300 by independently moving push rod 210 forward such that the push rod travels out of the syringe barrel 206, engages object 118, and moves object 118 to a position substantially adjacent the distal tip of needle 102. For example, the object 118 may be disposed immediately behind an initial bevel of sharp end 104 in the armed state. The position of the push rod 210 relative to the position of plunger 206 for drawing a particular amount of fluid (e.g., 1 cc) and for accomplishing this disposition of object 118 is indicated on the push rod with a marker 302. At this point, the user may make the injection into the patient by piercing sharp end 104 into the patient's tissue until the needle tip has reached a desired location. The user then delivers the solid object 118 and injects the fluid 214 by moving push rod 210 through the rest of its travel until its lip 218 abuts against the rear face 220 of plunger 206, and then by moving plunger 206 and push rod 210 together to the end of their travel when the plunger bottoms out at the distal end of the syringe interior.

Figure 5:
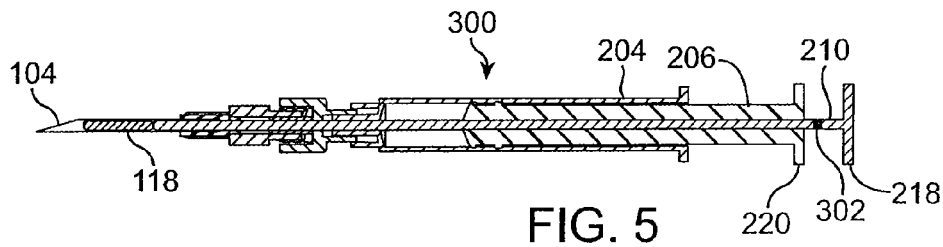
FIG. 5 illustrates the combined device in accordance with an embodiment of the present invention with the push rod and the object moved to the armed position.
Figure 6:
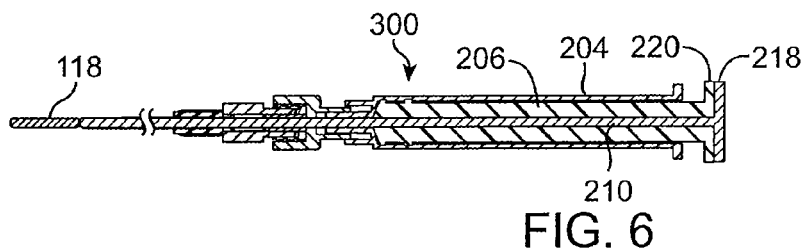
FIG. 6 illustrates a combined device in accordance with an embodiment of the present invention in the final state with the plunger and the push rod distally pushed to the end of their travels, the object and the fluid having been ejected from the distal end of the needle.

In one preferred embodiment, a movement of push rod 210, from its marker position shown in FIG. 5 to the position where lip 218 abuts against the rear face 220 of plunger 206 when the plunger has drawn a set amount of fluid (e.g., 1 cc), effectively ejects object 118 out of needle 102 and into the patient. The subsequent movement of push rod 210 together with plunger 206 may cause the distal tip of the push rod to push object 118 further into the placement site and effectively ejects fluid 214 from the syringe.

In an alternatively method of operation, the user may make the injection into the patient when device 300 is configured as shown in FIG. 4. In this approach, the delivery of object 118 and injection of fluid 214 is accomplished after the needle is in place by one continuous forward movement of the user against lip 218 of push rod 210, which moves the push rod distally independent of plunger 206 until the push rod abuts against the rear face 220 of the plunger. The plunger 206 is then moved distally to the end of its travel together with push rod 210 to inject fluid 214.

Applications of the present invention are numerous and are not limited to those presently contemplated. Regardless, some exemplary applications are described. One particular application, as mentioned above, is the simultaneous delivery of an animal identification transponder with a fluid (e.g., an anti-biotic to prevent infection at the delivery site, a vaccine, or other medication, which may be needed by the animal in any event). Recently, animal identification has made use of electronic markers injected into the animal. For example, U.S. Pat. Nos. 4,730,188 and 5,041,826, the disclosures of which are incorporated herein by reference, refer to passive integrated transponders disposed or embedded in a glass or plastic tube. Once delivered, the transponder can be excited by inductive coupling from an interrogator held or positioned on the exterior of the animal in the general vicinity of the transponder in its tissue. The transponder responds to the interrogator via the inductive coupling with a signal constituting a stream of data unique to the transponder in question, which data identifies the animal in which the transponder has been delivered.

Similarly, micro-chips or other devices, such as near-field RFID devices, may be delivered into human or animal patients using the present invention along with fluid antibiotics or pain killers. Presently, the FDA has approved similar devices for human use for identification, medical records, wandering patients, infant ID, etc. In another application, collagen wound fillers or biopsy markers (collagen plus radio-opaque marker) may be placed using the present invention along with fluids for immediately wetting and expanding the collagen plug and/or fluid medications. As such, application of the present invention enables delivery of two separate agents that the user desires to keep apart until they are mixed in-situ. With collagen plugs, due to their dissolution and expansion upon contact with moisture, it is desirable that the plug be kept apart from a wetting fluid until the plug has been placed. Similarly, the present invention may be used to deliver a fluid-filled capsule or a solid caplet of a first agent/medication, which may then be mixed with a second agent/medication injected in fluid form, which may aid in the dissolution and time-release of the first agent and/or produce additional benefits caused by the mixing of the two agents. Alternatively, the agent injected in fluid form may be the same agent as that of the capsule/caplet and the fluid may serve to provide an immediate blood level for the agent while the capsule/caplet provides time release of a specific amount over time.

The foregoing describes some embodiments that implement the concepts of the present invention. The description is for purposes of illustration and not limitation. Modifications of the above embodiments that are within the ordinary skill of the art are fully contemplated and encompassed by the scope of the present invention, which is limited only by the appended claims.

What is claimed is:

1. An injector for simultaneously co-injecting an object and an amount of fluid, the injector comprising:
   a syringe portion comprising a barrel, a plunger, and a push rod coaxially disposed about an axis, wherein the plunger includes a hollow channel that extends over the full length of the plunger and the push rod is movably disposed in the channel so that ends of the push rod can extend past respective ends of the channel, the push rod and the plunger being movable along the axis independently of each other, the barrel holding the amount of fluid in a space created by movement of the plunger along the axis;
   a needle portion comprising a needle for penetrating tissue and forming an opening in the tissue, the needle portion being configured to hold the object and allow the object to be ejected from a distal end of the needle,
   wherein the needle portion is separably coupled with the syringe portion,
   wherein the push rod is configured to move distally along the axis to engage the object held in the needle portion and to eject the object from the distal end of the needle, and
   wherein the plunger is configured to move distally along the axis to eject the amount of fluid out of the distal end of the needle past the opening formed in the tissue by the needle.

2. The injector of claim 1, wherein the needle portion further comprises a housing disposed proximally of the needle configured to hold the object entirely within the housing.

3. The injector of claim 2, wherein the object is secured within the housing with an adhesive.

4. The injector of claim 2, wherein the object is secured within the housing a press fit between the object and the housing.

5. The injector of claim 1, wherein the push rod is configured to move distally independent of the plunger until a rear lip of the push rod abuts a rear end of the plunger, and wherein the push rod and the plunger are configured to thereafter move together in the distal direction.

6. The injector of claim 1, wherein the needle includes a sharp end configured to penetrate tissue.

7. The injector of claim 1, wherein the amount of fluid held in the barrel is 1 ml or more.

8. The injector of claim 7, wherein the injector is configured to eject the object when the push rod is moved distally to abut a rear face of the plunger.

9. The injector of claim 7, wherein a distance between a rear lip of the push rod and a rear face of the plunger that places the object substantially adjacent a distal end of the needle is indicated on the push rod.

10. The injector of claim 1, wherein the object is one of an electronic marker or transponder, a plug of collagen, a caplet of medication, a pellet containing a fluid, a solid, semi-solid, or gel.

11. The injector of claim 1, wherein the syringe portion includes a distal end configured to couple with a proximal end of the needle portion to create a fluid-tight connection.

12. The injector of claim 11, wherein the connection is created using a luerlock.

13. An injector for simultaneously co-injecting an object and an amount of fluid, the injector comprising:

a syringe portion comprising a barrel, a plunger, and a push rod coaxially disposed about an axis, the plunger including a hollow channel extending over the length of the plunger in which the push rod is received and movable relative to the plunger so that a distal end of the push rod can be extended past a distal end of the plunger, the push rod and the plunger being movable along the axis independently of each other, the barrel holding the amount of fluid in a space created by movement of the plunger along the axis, the push rod and the plunger being movable along the axis independently of each other, the barrel holding the amount of fluid in a space created by movement of the plunger along the axis;

a needle portion comprising a needle and a housing configured to hold the object, wherein the needle portion is configured to allow the object to pass from the housing and out of a distal end of the needle, wherein the needle portion is separably coupled with the syringe portion, wherein the push rod is configured to move distally along the axis to engage the object held in the needle portion and to eject the object from the distal end of the needle, and wherein the plunger is configured to move distally along the axis to eject the amount of fluid out of the distal end of the needle.

* * * * *